United States Patent
Hibst et al.

(10) Patent No.: US 6,921,836 B1
(45) Date of Patent: Jul. 26, 2005

(54) MULTIMETAL OXIDE MATERIALS

(75) Inventors: Hartmut Hibst, Schriesheim (DE); Signe Unverricht, Mannheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/646,877

(22) PCT Filed: Mar. 26, 1999

(86) PCT No.: PCT/EP99/02085
§ 371 (c)(1),
(2), (4) Date: Oct. 5, 2000

(87) PCT Pub. No.: WO99/51343
PCT Pub. Date: Oct. 14, 1999

(30) Foreign Application Priority Data

Apr. 6, 1998 (DE) .......................... 198 15 281

(51) Int. Cl.$^7$ .................... C07C 51/235; B01J 23/00
(52) U.S. Cl. .................. 562/535; 562/532; 502/312
(58) Field of Search ................. 562/532, 535; 502/312

(56) References Cited

U.S. PATENT DOCUMENTS

| | | |
|---|---|---|
| 4,075,127 A | 2/1978 | Kadowaki et al. |
| 4,469,357 A | 9/1984 | Martin |
| 5,446,004 A | 8/1995 | Tenten et al. |
| 5,493,052 A | 2/1996 | Tenten et al. |
| 5,686,373 A | 11/1997 | Tenten et al. |
| 5,739,392 A | 4/1998 | Tanimoto et al. |
| 5,885,922 A | 3/1999 | Hibst et al. |

FOREIGN PATENT DOCUMENTS

| | | |
|---|---|---|
| DE | 24 07 677 | 8/1975 |
| DE | 26 35 031 A | 7/1977 |
| DE | 44 05 060 | 8/1995 |
| EP | 0 235 760 | 9/1987 |
| EP | 0 668 104 A | 8/1995 |
| EP | 0 686 600 | 12/1995 |
| EP | 0 758 562 A | 2/1997 |
| EP | 0 811 597 A | 12/1997 |

Primary Examiner—Paul A. Zucker
(74) Attorney, Agent, or Firm—Oblon, Spivak, McClelland, Maier & Neustadt, P.C.

(57) ABSTRACT

Multimetal oxide materials containing molybdenum, vanadium, copper and antimony and one or more specific other metals and having a multicomponent structure are used for the gas-phase catalytic oxidative preparation of acrylic acid from acrolein.

4 Claims, No Drawings

MULTIMETAL OXIDE MATERIALS

This application is a 371 of PCT/EP99/02085 filed Mar. 26, 1999.

SUMMARY OF THE INVENTION

The present invention relates to multimetal oxide materials of the formula I $$[A]_p[B]_q[C]_r \quad (I),$$

where
A is $Mo_{12}V_aX^1_bX^2_cX^3_dX^4_eX^5_fX^6_gO_x$,
B is $X^7_1Cu_hH_iO_y$,
C is $X^8_1Sb_jH_kO_z$,
$X^1$ is W, Nb, Ta, Cr and/or Ce, preferably W, Nb and/or Cr,
$X^2$ is Cu, Ni, Co, Fe, Mn and/or Zn, preferably Cu, Ni, Co and/or Fe,
$X^3$ is Sb and/or Bi, preferably Sb,
$X^4$ is Li, Na, K, Rb, Cs and/or H, preferably Na and/or K,
$X^5$ is Mg, Ca, Sr and/or Ba, preferably Ca, Sr and/or Ba,
$X^6$ is Si, Al, Ti and/or Zr, preferably Si, Al and/or Ti,
$X^7$ is Mo, W, V, Nb and/or Ta, preferably Mo and/or W,
$X^8$ is Cu, Ni, Zn, Co, Fe, Cd, Mn, Mg, Ca, Sr and/or Ba, preferably Cu and/or Zn, particularly preferably Cu,
a is from 1 to 8, preferably 2 to 6,
b is from 0.2 to 5, preferably from 0.5 to 2.5,
c is from 0 to 23, preferably from 0 to 4,
d is from 0 to 50, preferably from 0 to 3,
e is from 0 to 2, preferably from 0 to 0.3,
f is from 0 to 5, preferably from 0 to 2,
g is from 0 to 50, preferably from 0 to 20,
h is from 0.3 to 2.5, preferably from 0.5 to 2, particularly preferably from 0.75 to 1.5,
i is from 0 to 2, preferably from 0 to 1,
j is from 0.1 to 50, preferably from 0.2 to 20, particularly preferably from 0.2 to 5,
k is from 0 to 50, preferably from 0 to 20, particularly preferably from 0 to 12,
x,y and z are numbers which are determined by the valency and frequency of the elements other than oxygen in (I) and
p,q and r are numbers other than zero, with the proviso that the ratio p/(q+r) is from 20:1 to 1:20, preferably from 5:1 to 1:14, particularly preferably from 2:1 to 1:8, and the ratio q/r is from 20:1 to 1:20, preferably from 2:1 to 1:2, particularly preferably 1:1,
which contain the moiety $[A]_p$ in the form of three-dimensional regions A having the chemical composition $$Mo_{12}V_aX^1_bX^2_cX^3_dX^4_eX^5_fX^6_gO_x, \quad A$$

the moiety $[B]_q$ in the form of three-dimensional regions B having the chemical composition $$X^7_1Cu_hH_iO_y \text{ and} \quad B$$

the moiety $[C]_r$ in the form of three-dimensional regions C having the chemical composition $$X^8_1Sb_jH_kO_z \quad C$$

the regions A, B and C being distributed relative to one another in the same way as in a mixture comprising finely divided A, finely divided B and finely divided C.

The present invention furthermore relates to the use of multimetal oxide materials (I) for catalytic gas-phase oxidations of low molecular weight organic compounds, in particular of acrolein to acrylic acid, and processes for the preparation of multimetal oxide materials (I).

DESCRIPTION OF THE PRIOR ART

DE-A 44 05 514, DE-A 44 40 891, DE-A 19 528 646 and DE-A 19 740 493 relate to multimetal oxide materials which have a two-component structure $[A']_{p'}$ $[B']_{q'}$, the gross elemental compositions of component A' and of component B' there each corresponding to the gross elemental compositions of component A and of component B of the multimetal oxide materials (I) of the present invention.

However, the disadvantage of the abovementioned prior art multimetal oxide materials is that, when they are used as catalysts for the gas-phase catalytic oxidation of acrolein to acrylic acid, the selectivity of the acrylic acid formation at a given conversion is not completely satisfactory.

WO 96/27437 relates to multimetal oxide materials which contain the elements Mo, V, Cu and Sb as essential components and whose X-ray diffraction pattern has the line of strongest intensity at a 2θ-value of 22.2±0.3°. WO 96/27437 recommends these multimetal oxide materials as suitable catalysts for the gas-phase catalytic oxidation of acrolein to acrylic acid. Furthermore, WO 96/27437 recommends employing $Sb_2O_3$ as an antimony source for the preparation of these multimetal oxide materials. A prior preparation of an Sb-containing component is not described in WO 96/27437.

EP-B 235 760 relates to a process for the preparation of Sb-, Mo-, V- and/or Nb-containing multimetal oxide materials which are suitable as catalysts for the gas-phase catalytic oxidation of acrolein to acrylic acid. EP-B 235 760 recommends using an antimonate prepared beforehand as an antimony source for the preparation of these multimetal oxide materials. The prior preparation of a Cu-containing component is not described in EP-B 235 760.

The disadvantage of the multimetal oxide materials of WO 96/27437 and of EP-B 235 760 is that, when they are used as catalysts for the gas-phase catalytic oxidation of acrolein to acrylic acid, their activity and the selectivity of the acrylic acid formation are likewise not completely satisfactory.

OBJECT OF THE INVENTION

It is an object of the present invention to provide novel multimetal oxide materials which, when used as catalysts for the gas-phase catalytic oxidation of acrolein to acrylic acid, have the disadvantages of the catalysts of the prior art, if at all, at most to a smaller extent.

We have found that this object is achieved by the multimetal oxide materials (I) defined at the outset.

DETAILED DESCRIPTION OF THE INVENTION

Preferred multimetal oxide materials (I) are those whose regions A have a composition of the following formula II $$Mo_{12}V_{a'}X^1_{b'}X^2_{c'}X^5_{f'}X^6_{g'}O_{x'} \quad (II),$$

where
$X^1$ is W and/or Nb,
$X^2$ is Cu and/or Ni,
$X^5$ is Ca and/or Sr,
$X^6$ is Si and/or Al,
a' is from 2 to 6,
b' is from 1 to 2,
c' is from 1 to 3,
f' is from 0 to 0.75,
g' is from 0 to 10 and x' is a number which is determined by the valency and frequency of the elements other than oxygen in II.

It is also advantageous if the moieties $[B]_q$, $[C]_r$ of the novel multimetal oxide materials (I) are present in the latter in the form of three-dimensional regions of the chemical composition B, C, whose maximum diameters d (longest connecting line between two points present on the surface (interface) of the region and passing through the center of gravity of the region) are from >0 to 300 μm, preferably from 0.01 to 100 μm, particularly preferably from 0.05 to 20 μm. Of course, the maximum diameters may however also be from 0.01 to 150 μm or from 75 to 125 μm (the maximum diameter can be determined experimentally, for example, by a microstructure analysis by means of a scanning electron microscope (SEM)).

The moiety $[A]_p$ may be present in the novel multimetal oxide materials (I) in amorphous and/or crystalline form.

In principle, the moieties B and C, too, may be present in the novel multimetal oxide materials (I) in amorphous and/or crystalline form.

According to the invention, it is advantageous if the promoter phase B consists of crystallites of oxometallates B or contains such oxometallate crystallites B which have the X-ray diffraction pattern and hence the crystal structure type of at least one of the following copper molybdates (the expression in brackets gives the source of the associated X-ray diffraction fingerprint) or if the promoter phase B consists of crystallites of these copper molybdates or contains such copper molybdate crystallites:

$Cu_4Mo_6O_{20}$ [A. Moini et al., Inorg. Chem. 25 (21) (1986) 3782–3785], $Cu_4Mo_5O_{17}$ [index card 39-181 of the JCPDS-ICDD index (1991)], α-$CuMoO_4$ [index card 22-242 of the JCPDS-ICDD index (1991)], $Cu_6Mo_5O_{18}$ [index card 40-865 of the JCPDS-ICDD index (1991)], $Cu_{4-x}Mo_3O_{12}$ where x is from 0 to 0.25 [index card 24-56 and 26-547 of the JCPDS-ICDD index (1991)], $Cu_6Mo_4O_{15}$ [index card 35-17 of the JCPDS-ICDD index (1991)], $Cu_3(MoO_4)_2(OH)_2$ [index card 36-405 of the JCPDS-ICDD index (1991)), $Cu_3Mo_2O_9$ [index card 24-55 and 34-637 of the JCPDS-ICDD index (1991)], $Cu_2MoO_5$ (index card 22-607 of the JCPDS-ICDD index (1991)].

Advantageous according to the invention are moieties B which contain or consist of oxometallates B which have the X-ray diffraction pattern and hence the crystal structure type of the following copper molybdate or which contain or consist of this copper molybdate itself:

$CuMoO_4$-III having the wolframite structure according to Russian Journal of Inorganic Chemistry 36 (7) (1991), 927–928, Table 1.

Among these, those having the following stoichiometry III $$CuMo_AW_BV_CNb_DTa_EO_y \cdot (H_2O)_F \quad (III),$$

where
1/(A+B+C+D+E) is from 0.7 to 1.3, preferably from 0.85 to 1.15, particularly preferably from 0.95 to 1.05, very particularly preferably 1,
F is from 0 to 1,
B+C+D+E is from 0 to 1, preferably from 0 to 0.7, and
Y is a number which is determined by the valency and frequency of the elements other than oxygen,
are preferred.

Particularly preferred among these are those having the stoichio-metries IV, V or VI:

$$CuMo_AW_BV_CO_y \quad (IV),$$

where
1/(A+B+C) is from 0.7 to 1.3, preferably from 0.85 to 1.15, particularly preferably from 0.95 to 1.05, very particularly preferably 1,
B+C is from 0 to 1, preferably from 0 to 0.7, and
Y is a number which is determined by the valency and frequency of the elements other than oxygen;

$$CuMo_AW_BO_y \quad (V),$$

where
1/(A+B) is from 0.7 to 1.3, preferably from 0.85 to 1.15, particularly preferably from 0.95 to 1.05, very particularly preferably 1,
A and B are each from 0 to 1 and
Y is a number which is determined by the valency and frequency of the elements other than oxygen;

$$CuMo_AV_CO_y \quad (VI),$$

where
1/(A+C) is from 0.7 to 1.3, preferably from 0.85 to 1.15, particularly preferably from 0.95 to 1.05, very particularly preferably 1,
A and C are each from 0 to 1 and
Y is a number which is determined by the valency and frequency of the elements other than oxygen.

The preparation of such oxometallates B is disclosed, for example, in EP-A 668 104.

Suitable promoter phases B are also those which contain or consist of the oxometallates B having the following stoichiometry VII $$CuMo_AW_BV_CNb_DTa_EO_y \quad (VII),$$

where
1/(A+B+C+D+E) is from 0.7 to 1.3, preferably from 0.85 to 1.15, particularly preferably from 0.95 to 1.05, very particularly preferably 1,
(B+C+D+E)/A is from 0.01 to 1, preferably from 0.05 to 0.3, particularly preferably from 0.075 to 0.15, very particularly preferably, 0.11, and
Y is a number which is determined by the valency and frequency of the elements other than oxygen,
of a structure type which was referred to as the HT copper molybdate structure and is defined below by its X-ray diffraction pattern (fingerprint), represented by its most characteristic and most intense diffraction lines in the form of interplanar spacings d [Å] independent of the wavelength of the X-rays used:

6.79±0.3
3.56±0.3
3.54±0.3
3.40±0.3
3.04±0.3
2.96±0.3
2.67±0.2
2.66±0.2
2.56±0.2

2.36±0.2
2.35±0.2
2.27±0.2
2.00±0.2
1.87±0.2
1.70±0.2
1.64±0.2
1.59±0.2
1.57±0.2
1.55±0.2
1.51±0.2
1.44±0.2.

Where the promoter phase B contains or consists of a mixture of different oxomettalates B, a mixture of oxomettallates having the wolframite and HT copper molybdate structure is preferred. The weight ratio of crystallites having the HT copper molybdate structure to crystallites having the wolframite structure may be from 0.01 to 100, from 0.1 to 10, from 0.25 to 4 and from 0.5 to 2.

The preparation of oxomettallates VII or materials containing them is disclosed, for example, in DE-A 19 528 646.

Those novel multimetal oxide materials whose regions C essentially comprise crystallites which have the trirutile structure type of α-and/or β-copper antimonate $CuSb_2O_6$ are particularly preferred. α-$CuSb_2O_6$ crystallizes in a tetragonal trirutile structure (E.-O. Giere et al., J. Solid State Chem. 131 (1997) 263–274), while β-$CuSb_2O_6$ has a distorted monoclinic trirutile structure (A. Nakua et al., J. Solid State Chem. 91 (1991), 105–112, or reference diffraction pattern in index card 17-284 in the JCPDS-ICDD index 1989). Regions C which have the pyrochlore structure of the mineral partzite, of a copper antimony oxide hydroxide with the variable composition $Cu_ySb_{2-x}(O, OH, H_2O)_{6-7}$ ($y \leq 2$, $0 \leq x \leq 1$) are also preferred (B. Mason et al., Mineral. Mag. 30 (1953), 100–112, or reference pattern in index card 7-303 of the JCPDS-ICDD index 1996).

Furthermore, the regions C may consist of crystallites which have the structure of copper antimonate $Cu_9Sb_4O_{19}$ (S. Shimada et al., Chem. Lett. 1983, 1875–1876, or S. Shimada et al., Thermochim. Acta 133 (1988), 73–77, or reference pattern in index card 45-54 of the JCPDS-ICDD index) and/or the structure of $Cu_4SbO_{4.5}$ (S. Shimada et al., Thermochim. Acta 56 (1982), 73–82, or S. Shimada et al., Thermochim. Acta 133 (1988), 73–77, or reference pattern in index card 36-1106 of the JCPDS-ICDD index).

The regions C can of course also consist of crystallites which are a mixture of the abovementioned structures.

The novel multimetal oxide materials (I) are obtainable in a simple manner, for example by preforming, in finely divided form, a multimetal oxide material $$X^7{}_1Cu_hH_iO_y \quad (B)$$

as starting material I and a multimetal oxide material $$X^8{}_1Sb_jH_kO_z \quad (C)$$

as starting material 2, either separately from one another or in association with one another, and then bringing the starting materials 1, 2 into intimate contact with suitable sources of the elemental constituents of the multimetal oxide material A $$Mo_{12}V_aX^1{}_bX^2{}_cX^3{}_dX^4{}_eX^5{}_fX^6{}_gO_x \quad (A)$$

in the desired ratio and calcining the resulting dry blend at from 250 to 500° C., it being possible to carry out the calcination under inert gas (e.g. $N_2$), a mixture of inert gas and oxygen (e.g. air), reducing gases, such as hydrocarbons (e.g. methane), aldehydes (e.g. acrolein) or ammonia, or under a mixture of $O_2$ and reducing gases (e.g. all of the abovementioned), as described, for example, in DE-A 43 35 973. In a calcination under reducing conditions it should be ensured that the metallic constituents are not reduced to the element.

The duration of calcination is as a rule from a few minutes to a few hours and usually decreases with increasing calcination temperature. As is generally known, what is important regarding the sources of the elemental constituents of the multimetal oxide material A is that they are either already an oxide or a compound which can be converted into oxides by heating, at least in the presence of oxygen. In addition to the oxides, particularly suitable starting compounds are halides, nitrates, formates, oxalates, citrates, acetates, carbonates and hydroxides.

Suitable starting compounds of Mo, V, W and Nb are also their oxo compounds (molybdates, vanadates, tungstates and niobates) or the acids derived therefrom. This applies in particular to the corresponding ammonium compounds (ammonium molybdate, ammonium vanadate, ammonium tungstate).

According to the invention, the finely divided starting materials 1, 2 advantageously consist of particles whose maximum diameter d (longest connecting line between two points present on the surface of the particle and passing through the center of gravity of the particle) is from >0 to 300 μm, preferably from 0.01 to 100 μm, particularly preferably from 0.05 to 20 μm. However, the particle diameters d can of course also be from 0.01 to 150 μm or from 75 to 125 μm.

It is possible that the starting materials 1, 2 to be used according to the invention have a specific surface area SSA (determined according to DIN 66131 by gas adsorption ($N_2$) according to Brunauer-Emmet-Teller (BET)) of $\leq 80$ m²/g, frequently $\leq 50$ m²/g or $\leq 10$ m²/g and in some cases $\leq 1$ m²/g. As a rule, the SSA is >0.1 m²/g.

According to the invention, the starting materials 1, 2 used may be in amorphous and/or crystalline form.

It is advantageous if the starting materials 1, 2 consist of crystallites of oxometallates B (for example those of the formulae III to VII) and crystallites of oxometallates C, as described above. As mentioned above, such oxomettallates B are obtainable, for example, by the procedures of EP-A 668 104 or DE-A 19 528 646. However, the preparation processes of DE-A 44 05 514 and DE-A 44 40 891 may also be used.

In principle, multimetal oxide materials B containing oxomettallates B or consisting of oxomettallates B can be prepared in a simple manner by producing a very intimate, preferably finely divided, dry blend having a composition corresponding to the stoichiometry of said multimetal oxide materials from suitable sources of the elemental constituents and calcining said dry blend at from 200 to 1000° C., preferably from 250 to 900° C. or from 700 to 850° C. for several hours under an inert gas or preferably in the air, it being possible for the duration of calcination to be from a few minutes to a few hours. The calcination atmosphere may additionally contain steam. Suitable sources of the elemental constituents of the multimetal oxide material B are compounds which are already oxides and/or compounds which can be converted into oxides by heating, at least in the presence of oxygen. In addition to the oxides, particularly suitable starting compounds of this type are halides, nitrates, formates, oxalates, citrates, acetates, carbonates, ammine complex salts, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ or ammonium oxalate, which decompose and/or can be decomposed at the latest during the subsequent calcination to give compounds escaping in gaseous form, may additionally be incorporated).

The intimate mixing of the starting compounds for the preparation of multimetal oxide materials B can be carried out in dry form or in wet form. If it is effected in dry form, the starting compounds are advantageously used in the form of finely divided powder and are subjected to the calcination after the mixing and any compaction. However, intimate mixing is preferably effected in wet form. Usually, the starting compounds are mixed with one another in the form of an aqueous solution and/or suspension. Particularly intimate dry blends are obtained in the drying method described when exclusively dissolved sources of the elemental constituents are used as starting materials. The preferably used solvent is water. The aqueous material obtained is then dried, the drying process preferably being effected by spray-drying of the aqueous mixture with outlet temperatures of from 100 to 150° C. The dry material is then calcined as described above.

A preferred method of preparation of oxometallates B ($X^7{}_1Cu_hH_iO_y$, where X is Mo and/or W) comprises adding an aqueous ammoniacal solution of copper carbonate (for example having the composition $Cu(OH)_2CO_3$) to an aqueous solution of ammonium heptamolybdate and ammonium paratungstate, drying, for example spray-drying, the resulting mixture and calcining the resulting dry blend as described, if required after subsequent kneading and extrusion as well as drying.

In another method of preparation of the multimetal oxide materials B, the thermal treatment of the mixture of the starting compounds used is carried out in a vessel (autoclave) in the presence of steam at superatmospheric pressure at from >100 to 600° C. The pressure range typically extends up to 500, preferably up to 250, atm. This hydrothermal treatment is particularly advantageously carried out at from >100 to 374.15° C. (critical temperature of water), in which steam and liquid water coexist under the resulting pressures.

The multimetal oxide materials B obtainable as described above, which may contain oxometallates B of a single structure type or a mixture of oxometallates B of different structure types, or consist exclusively of oxometallates. B of a single structure type or a mixture of oxometallates of different structure types, can be used as starting material 1 required according to the invention, if necessary after milling and/or classification to the desired sizes.

The multimetal oxide materials C can in principle be prepared in the same way as the multimetal oxide materials B. In the case of the multimetal oxide material C, the calcination of the intimate dry blend is advantageously carried out at from 250 to 1200° C., preferably from 250 to 50° C. The calcination can be effected under an inert gas or under a mixture of an inert gas and oxygen, e.g. air, or under pure oxygen. Calcination under a reducing atmosphere is likewise possible. Here too, the required calcination time generally decreases with increasing calcination temperature.

Multimetal oxide materials C preferably used according to the invention are those which are obtainable by preparing a dry blend from sources of the elemental constituents of the multimetal is oxide material C which contain at least a part, preferably the total amount, of the antimony in oxidation state +5 and calcining said dry blend at from 200 to 1200° C., preferably from 200 to 850° C., particularly preferably from 300 to 850° C. Such multimetal oxide materials C are obtainable, for example, by the preparation methods described in detail in DE-A 24 07 677. The preferred procedure among these is the one in which antimony trioxide or $Sb_2O_4$ is oxidized in an aqueous medium by means of hydrogen peroxide in an amount which is less than the stoichiomeric amount or equal to it or greater than it, and from 40 to 100° C. to give antimony (V) oxide hydroxide, aqueous solutions and/or suspensions of suitable starting compounds or the other elemental constituents of the multimetal oxide material C are added before this oxidation, during this oxidation and/or after this oxidation, the resulting aqueous mixture is then dried (preferably spray-dried, inlet temperature: from 250 to 600° C., outlet temperature: from 80 to 130° C.) and the intimate dry blend is then calcined as described.

In the process just described, for example, aqueous hydrogen peroxide solutions having an $H_2O_2$ content of 5 to 33% by weight may be used. Subsequent addition of suitable starting compounds of the other elemental constituents of the oxometallate C is advisable in particular when they are capable of catalytically decomposing the hydrogen peroxide. However, it would of course also be possible to isolate the antimony of (V) oxide hydroxide from the aqueous medium and to mix it intimately, for example, with suitable finely divided starting compounds of the other elemental constituents of the oxometallate C and, if required, further antimony starting compounds and then to calcine this intimate mixture as described.

What is important is that the sources of the elements of the oxometallates C are either already oxides or can be converted into such oxides by heating, if required in the presence of oxygen. In addition to the oxides, particularly suitable starting compounds are therefore halides, nitrates, formates, oxalates, acetates, carbonates and/or hydroxides (compounds such as $NH_4OH$, $(NH_4)_2CO_3$, $NH_4NO_3$, $NH_4CHO_2$, $CH_3COOH$, $NH_4CH_3CO_2$ or ammonium oxalate, which decompose and/or can be decomposed at the latest during the subsequent calcination to give compounds escaping in gaseous form, may additionally be incorporated).

For the preparation of oxometallates C, it is in general also possible to carry out the intimate mixing of the starting compounds in dry or in wet form. If it is effected in dry form, the starting compounds are advantageously used in the form of finely divided powders. However, the intimate mixing is preferably carried out in wet form. Usually, the starting compounds are mixed with one another in the form of an aqueous solution and/or suspension. After completion of the mixing process, the fluid material is dried and is calcined after the drying. Here too, the drying is preferably effected by spray-drying. After calcination is complete the oxometallates C can again be comminuted (for example by wet or dry milling, e.g. in a ball mill or by jet milling) and the particle class having a maximum particle diameter in the maximum diameter range desired for the novel multimetal oxide (I) can be separated off from the powder obtainable thereby and consisting as a rule of essentially spherical particles, by classification to be carried out in a manner known per se (for example wet or dry sieving). A preferred method of preparation of oxometallates C of the formula $(Cu,Zn)_1Sb_hH_iO_y$ comprises first converting antimony trioxide and/or $Sb_2O_4$ in an aqueous medium by means of hydrogen peroxide into a preferably finely divided Sb(V) compound, for example hydroxylated antimony (V) oxide hydroxide, adding an ammoniacal aqueous solution of zinc carbonate and/or copper carbonate (which may have, for example, the composition $Cu_2(OH)_2CO_3$) to the resulting aqueous suspension, drying the resulting aqueous mixture, for example spray-drying it in the manner described, and calcining the resulting powder as described, if required after subsequent kneading with water followed by extrusion and drying. Under advantageous conditions, the oxometallates B and the oxometallates C can be prepared in the form associated with one another. In these cases, a mixture of crystallites of the oxometallates B and of crystallites of the oxometallates C is obtained, which mixture can be used directly as starting material 1+2.

The components of the starting materials 1, 2 can be brought into contact with the sources of the multimetal oxide material A (starting material 3) either in dry or in wet form. In the latter case, all that is necessary is to ensure that the preformed crystallites B and crystallites C do not go into solution. In an aqueous medium, the latter is usually ensured at a pH which does not differ too greatly from 7 and at temperatures which are not too high. If the bringing into intimate contact is effected in wet form, drying to give a dry material is usually carried out subsequently (preferably by spray-drying). Such a dry material is automatically obtained in dry blending. The components of the starting materials 1, 2 can of course also be brought into intimate contact with the sources of the multimetal oxide material A (starting material 3) by a procedure in which first the oxometallates B and then the oxometallates C, or vice versa, are brought into contact. However, the multimetal oxide materials B and C can of course also be brought into intimate contact in the form of premixed starting material 1+2 with the components of the starting material 3.

Examples of suitable methods of mixing are:
a) mixing a dry, finely divided, preformed starting material 1+2 with dry, finely divided starting compounds of the elemental constituents of the desired multimetal oxide A in the desired ratio in a mixer, kneader or mill;
b) preforming a finely divided multimetal oxide A by intimate mixing of suitable starting compounds of its elemental constituents (dry or wet) and then calcining the resulting intimate dry blend at from 250 to 500° C.; converting the preformed multimetal oxide A into finely divided form and mixing it with the finely divided starting materials 1, 2 in the desired ratio as in a); in this method of mixing, the final calcination of the resulting mixture is not essential;
c) stirring the required amounts of preformed starting materials 1, 2 into an aqueous solution and/or suspension of starting compounds of the elemental constituents of the desired multimetal oxide A and then carrying out spray-drying; instead of the starting compounds of the elemental constituents of the desired multimetal oxide A, it is of course also possible to use a multimetal oxide A itself that is preformed according to b). Furthermore, in addition to the starting materials 1, 2 and the starting material 3, compounds such as $NH_4OH$, $(NH_4)_2CO_3$, $NH_4HCO_3$, $NH_4NO_3$, $NH_4CHO_2$, $CH_3COOH$ or $NH_4CH_3CO_2$, which decompose and/or can be decomposed at the latest during the subsequent calcination to give compounds escaping completely in gaseous form, can also be incorporated into the aqueous mixture.

Starting from the abovementioned sources of the elemental constituents, it is as a rule necessary to use elevated temperatures for the preparation of an aqueous solution required as starting material 3. As a rule, temperatures $\geq 60°$ C., in general $\geq 70°$ C., but usually $\leq 100°$ C. are used. The above and following statements are applicable in particular when ammonium heptamolybdate tetrahydrate [AHM= $(NH_4)_6Mo_7O_{24} \cdot 4\ H_2O$] is used as the source of elemental Mo and/or ammonium metavanadate [AMV=$NH_4VO_3$] is used as the vanadium source. The conditions are particularly difficult when the element W is a component of the aqueous starting material 3 and ammonium paratungstate heptahydrate [APW=$(NH_4)_{10}W_{12}O_{41} \cdot 7\ H_2O$] is used as a starting compound of the relevant aqueous solution in addition to at least one of the two abovementioned elemental sources.

It has now been found, surprisingly, that aqueous solutions prepared at elevated temperatures as starting material 3 are usually stable during and after the subsequent cooling below the dissolution temperature, even in the case of contents of elemental Mo of $\geq 10\%$ by weight, based on the aqueous solution, and cooling temperatures down to 20° C. or below (generally not $\leq 0°$ C.), i.e. no solid is precipitated during or after the cooling of the aqueous solution. The above statement also applies as a rule in the case of Mo contents up to 20% by weight, based on the aqueous solution.

Usually, the Mo content of such aqueous solutions cooled to 20° C. or below (generally not below 0° C.), and suitable as starting material 3, is not more than 35% by weight, based on the solution.

The above finding is due to the fact that the solution at elevated temperature evidently gives rise to compounds of the relevant elements which have high water solubility. This concept is supported by the fact that the residue obtainable from such an aqueous solution by drying (e.g. spray-drying) also has a correspondingly high solubility in water (even at the corresponding low temperatures).

Advantageously, the following procedure is therefore followed. An aqueous solution suitable as starting material 3 is produced at a temperature $T_L \geq 60°$ C. (e.g. at up to 65° C., or at up to 75° C., or at up to 85° C., or at up to 95° C. or at $\leq 100°$ C.). The finely divided solid starting materials 1, 2 are then incorporated into this aqueous solution, after cooling to a temperature $T_E < T_L$. Frequently, $T_L > 70°$ C. and $T_E \leq 70°$ C. If slightly lower dissolution rates and lower solids contents are accepted, however, $T_L \leq 60°$ C. is also possible.

The incorporation of the pre-prepared solid starting materials 1, 2 into the aqueous starting material 3 is usually carried out by addition of the starting materials 1, 2 to the aqueous starting material 3 cooled as described above and subsequent mechanical mixing, for example with the use of stirring aids or dispersants, over a period of from a few minutes or hours to several days, preferably over a period of several hours. As mentioned above, it is particularly advantageous according to the invention that the incorporation of solid starting materials 1, 2 into the aqueous starting material 3 is carried out at $\leq 70°$ C., preferably $\leq 60°$ C., particularly preferably $\leq 40°$ C. As a rule, the temperature of incorporation is $\geq 0°$ C.

It is furthermore advantageous if the solid starting materials 1, 2 are incorporated into an aqueous starting material 3 whose pH at 25° C. is from 4 to 7, preferably from 5 to 6.5. The latter can be achieved, for example, by adding one or more pH buffer systems to the aqueous starting material 3. Suitable as such is, for example, the addition of ammonia and acetic acid and/or formic acid or the addition of ammonium acetate and/or ammonium formate. Regarding the abovementioned intended use, it is of course also possible to use ammonium carbonate.

The aqueous mixture obtained on incorporating the starting materials 1, 2 into the aqueous starting material 3 is usually dried by spray-drying. Advantageously, outlet temperatures of from 100 to 150° C. are set. Spray-drying can be carried out by either the cocurrent or the countercurrent methods.

It is of course also possible to use all mixing variants between a), b), and/or c). The resulting intimate dry blend can then be calcined as described and thereafter shaped to give the desired catalyst geometry, or vice versa. In principle, the calcined (or optionally uncalcined when mixing variant b) is used) dry blend can however also be used in the form of a powder catalyst.

Our own investigations have shown that, on calcination of the dry blend comprising the starting materials 1, 2 and the starting material 3, the structure type of the crystallites contained in the starting materials 1, 2 is essentially retained or at most is converted into other structure types. However, fusion of the components of the starting materials 1, 2 with one another (dissolution in one another) or with those of the starting material 3 essentially does not take place.

As indicated above, this opens up the possibility, after milling of the preformed starting materials 1, 2, of separating off the particle class having a maximum particle diameter (as a rule from >0 to 300 $\mu$m, preferably from 0.01 to 100 $\mu$m, particularly preferably from 0.05 to 20 $\mu$m) within the maximum diameter range desired for the multimetal oxide material (I) by classification (e.g. wet or dry sieving) to be carried out in a manner known per se, and thus to use said particle class in a tailored manner for the preparation of the desired multimetal oxide material.

When the novel multimetal oxide materials (I) are used as catalysts for the gas-phase catalytic oxidation of acrolein to acrylic acid, the shaping to give the desired catalyst geometry is preferably carried out by application to preformed inert catalyst carriers, it being possible to effect the application before or after the final calcination. Usual carrier materials, such as porous or nonporous aluminas, silica, thorium dioxide, zirconium dioxide, silicon carbide or silicates, such as magnesium silicate or aluminium silicate, may be used. The supports may have a regular or irregular shape, regularly shaped supports having a pronounced surface roughness, for example spheres or hollow cylinders, being preferred. Among these, in turn, spheres are particularly advantageous. The use of essentially nonporous, spherical steatite carriers which have a rough surface and whose diameter is from 1 to 8 mm, preferably 4 to 5 mm, is particularly advantageous. The layer thickness of the active materials is advantageously chosen in the range from 50 to 500 $\mu$m, preferably from 150 to 250 $\mu$m. It should be pointed out here that, in the preparation of such coated catalysts, the powder material to be applied is as a rule moistened for coating the supports and is dried again after the application, for example by means of hot air.

The coating of the supports for the preparation of the coating catalysts is carried out as rule in a suitable rotatable container, as previously disclosed, for example, in DE-A 29 096 71 or in EP-A 293 859. As a rule, the relevant material is calcined before coating of the carriers.

The coating and calcination process according to EP-A 293 859 can be used in a suitable manner known per se so that the resulting multimetal oxide active materials (I) have a specific surface area of from 0.50 to 150 m$^2$/g, a specific pore volume of from 0.10 to 0.90 cm$^3$/g and a pore diameter distribution such that at least 10% of the total pore volume are in each of the diameter ranges from 0.1 to <1 $\mu$m, from 1.0 to <10 $\mu$m and 10 $\mu$m to 100 $\mu$m. It is also possible to establish the pore diameter distributions stated as being preferred in EP-A 293 859.

The novel multimetal oxide materials (I) can of course also be operated as unsupported catalysts. In this context, the intimate dry blend comprising the starting materials 1, 2 and 3 is preferably compacted directly to give the desired catalyst geometry (for example by means of pelleting or extrusion), it being possible, if required, to have conventional assistants, for example graphite or stearic acid as lubricants and/or molding assistants and reinforcing materials, such as microfibers of glass, asbestos, silicon carbide or potassium titanate added, and calcined. Here too, calcination can also be effected prior to shaping. A preferred geometry for unsupported catalysts is a hollow cylinder having an external diameter and a length of from 2 to 10 mm or from 3 to 8 mm and a wall thickness of from 1 to 3 mm.

The novel multimetal oxide materials (I) are particularly suitable as catalysts having high activity and selectivity (with a given conversion) for the gas-phase catalytic oxidation of acrolein to acrylic acid. Usually, acrolein which was produced by the catalytic gas-phase oxidation of propene is used in the process. As a rule, the acrolein-containing reaction gases of this propene oxidation are used without intermediate purification. The gasphase catalytic oxidation of the acrolein is usually carried out in tube-bundle reactors as a heterogeneous fixed-bed oxidation. Oxygen, advantageously diluted with inert gases (for example in the form of air), is used as an oxidizing agent in a manner known per se. Suitable diluent gases are, for example, $N_2$, $CO_2$, hydrocarbon, recycled reaction exit gases and/or steam. As a rule, an acrolein:oxygen:steam:inert gas volume ratio of 1:(1 to 3):(0 to 20):(3 to 30), preferably of 1:(1 to 3):(0.5 to 10):(7 to 18), is established in the acrolein oxidation. The reaction pressure is in general from 1 to 3 bar and the total space velocity is preferably from 1,000 to 3,500 l (S.T.P.) per 1 per h./l/h. Typical multitube fixed-bed reactors are described, for example, in DE-A 28 30 765, DE-A 22 01 528 or US-A 3 147 084. The reaction temperature is usually chosen so that the acrolein conversion in a single pass is above 90%, preferably above 98%. Usually, reaction temperatures are from 230 to 330° C. are required for this.

In addition to the gas-phase catalytic oxidation of acrolein to acrylic acid, the novel products are also capable of catalyzing the gas-phase catalytic oxidation of other organic compounds, in particular other alkanes, alkanols, alkanals, alkenes and alkenols, preferably of 3 to 6 carbon atoms (e.g. propylene, methacrolein, tert-butanol, the methyl ether of tert-butanol, isobutene, isobutane or isobutyraldehyde), to olefinically unsaturated aldehydes and/or carboxylic acids, and the corresponding nitriles (ammoxidation, especially of propene to acrylonitrile and of isobutene or tert-butanol to methacrylonitrile). The preparation of acrolein, methacrolein and methacrylic acid may be mentioned by way of example. However, they are also suitable for the oxidative dehydrogenation of olefinic compounds.

Unless stated otherwise, the conversion, selectivity and residence time in this publication are defined as follows:

$$\text{Conversion based on } U \text{ acrolein (\%)} = \frac{\text{number of moles of acrolein converted}}{\text{number of moles of acrolein used}} \times 100;$$

$$\text{Selectivity } S \text{ of the acrylic acid formation (\%)} = \frac{\text{number of moles of acrolein coverted into acrylic acid}}{\text{total number of moles of acrolein converted}} \times 100;$$

$$\text{Residence time (sec)} = \frac{\text{empty reactor volume filled with catalyst (1)}}{\text{synthesis gas throughput (l(S.T.P.)/h)}} \times 3{,}600.$$

EXAMPLES a) Preparation of novel multimetal oxide materials M and multimetal oxide materials MV for comparison and coated catalysts prepared from these multimetal oxide materials

Example 1

Preparation of the Starting Material 1:

219.9 g of ammonium heptamolybdate tetrahydrate (81.8% by weight of $MoO_3$) and 325.6 g of ammonium paratungstate heptahydrate (89.0% by weight of $WO_3$) were dissolved in succession in 5,000 g of water (solution a). 445.0 g of 25% strength by weight aqueous ammonia solution were added at 25° C. to 3,000 g of water and then 497.2 g of copper acetate hydrate (40.0% by weight of CuO) were dissolved therein, a deep blue solution being formed (solution b). Solution b was then stirred into solution a at 95° C., the temperature of the total mixture not falling below 80° C. The resulting aqueous suspension c was stirred for a further hour at 80° C. and then spray-dried (inlet temperature: 330° C., outlet temperature: 110° C.). The resulting light green spray-dried powder was kneaded with water in an LUK 2.5 kneader from Werner & Pfleiderer, Stuttgart, (200 g of water per kg of spray-dried powder) and molded on an extruder from Werner & Pfleiderer, Stuttgart, at 50 bar to give 6 mm thick extrudates (about 1 cm long). These extrudates were dried for 16 hours at 110° C. in air. The extrudates were then calcined under air. For this purpose, the material to be calcined (150 g) was introduced into a muffle furnace (internal volume: 3.0 l) at 200° C., through which 50 l (S.T.P)/h of air flowed, and was heated to 300° C. in the course of 1 hour, and left at this temperature for minutes, heated to 750° C. in the course of 2 hours and left at this temperature for 1 hour. The resulting product had a red-brown colour and, after milling in a centrifugal mill from Retsch, Germany, had a specific BET surface area according to DIN 66131 of 0.6±0.2 $m^2/g$ and the composition $CuMo_{0.5}W_{0.5}O_y$. With the use of Cu-Kα radiation (Siemens diffractometer D-5000, 40 kV, 30 mA, with automatic collimator and counter aperture and Peltier detector), the resulting crystalline powder of the composition $CuMo_{0.5}W_{0.5}O_y$ ($y \leq 4$) exhibited an X-ray powder diffraction pattern with superposition of the wolframite fingerprint and of the HT copper molybdate fingerprint, i.e. it had a two-phase structure. According to the line intensities, the two structure types were present roughly in the molar frequency ratio of 90 (wolframite structure): 10 (HT copper molybdate structure).

Preparation of the Starting Material 2:

946.0 g of $Sb_2O_3$ having an Sb content of 83.0% by weight were suspended in 4000 g of water while stirring. At room temperature (25° C.), 822.4 g of a 30% strength by weight aqueous $H_2O_2$ solution were added. The aqueous suspension was then heated to 100° C. in the course of 1 hour with further stirring and was refluxed at this temperature for 5 hours. A solution of 595.6 g of copper acetate hydrate (32.0% by weight of Cu) in 4000 g of water was then added to the aqueous suspension at 100° C. in the course of 30 minutes, the temperature of the suspension decreasing to 60° C. At this temperature, 407.9 g of a 25% strength aqueous ammonia solution were then added. Thereafter, the aqueous suspension was stirred for a further 2 hours at 80° C. and cooled to room temperature (25° C.). Finally, the aqueous suspension was spray-dried (inlet temperature: 350° C., outlet temperature: 110° C.). In a rotary furnace (1.5 l internal volume) with a capacity of 50 l (S.T.P.)/h of air, a part of the resulting spray-dried powder (150 g) was heated stepwise to 150° C. in the course of 1 hour, then to 200° C. in the course of 4 hours and then to 300° C. in the course of 2 hours and was kept at the last-mentioned temperature for 1 hour. Thereafter, the powder was heated to 800° C. in the course of 2 hours and kept at this temperature for 2 hours. The resulting powder had a specific BET surface area of 0.6 $m^2/g$ and the composition $CuSb_{2.15}O_z$ ($z \leq 0.6375$). The powder X-ray pattern of the powder obtained exhibited essentially the diffraction reflections of the $CuSb_2O_6$ (reference spectrum 17-0284 of the JCPDS-ICDD index).

Preparation of the Starting Material 3:

703.6 g of ammonium heptamolybdate tetrahydrate (81.8% by weight of $MoO_3$), 135.72 g of ammonium metavanadate (77.3% by weight of $V_2O_5$) and 120.3 g of ammonium paratungstate heptahydrate (89.0% by weight of $WO_3$) were dissolved in succession in 5170 g of water at 95° C. The aqueous solution (starting material 3) was thus based on the following elemental stoichiometry:

$$Mo_4V_{1.15}W_{0.46} \hat{=} (Mo_{12}V_{3.46}W_{1.38})_{0.33}.$$

Preparation of the Multimetal Oxide Material M1 and of the Coated Catalyst SM1:

The clear, orange aqueous solution obtained above (starting material 3) was cooled to 25° C., after which 116.9 g of 100% strength by weight acetic acid and 132.3 g of 25% strength by weight aqueous ammonia solution were added in succession. 82.3 g of starting material 1 were stirred into the aqueous solution cooled to 25° C. and containing starting material 3, so that the molar ratio of the abovementioned stoichiometric units was 0.31 (starting material 1) to 0.33 (starting material 3). 129.7 g of starting material 2 were then added to the aqueous suspension containing starting materials 1 and 3, so that the molar ratio of the abovementioned stoichiometric units was 0.30 (starting material 2) to 0.33 (starting material 3). The resulting aqueous suspension was stirred for a further hour at 25° C. and the aqueous mixture was then spray-dried (inlet temperature: 350° C., outlet temperature: 110° C.). The spray-dried powder was then kneaded with a mixture of 70% by weight of water and 30% by weight of acetic acid (0.35 kg of liquid/kg of spray-dried powder) (LUK 2.5 kneader from Werner & Pfleiderer, Stuttgart). The kneaded material obtained was dried for 16 hours at 110° C. in a through-circulation oven. The comminuted kneaded material was calcined in a cylindrical rotating tube (internal diameter 12.5 cm, heated length 51 cm) through which 10 l (S.T.P.)/h of air flowed. 700 g of material to be calcined were introduced into the heated zone of the rotating tube. During the calcination, the kneaded material was first heated to 210° C. in the course of 30 minutes, the temperature was then increased to 310° C. in the course of 2.5 hours and said material was then heated to 395° C. in the course of 2.5 hours and this temperature was maintained for 3 hours. The resulting catalytically active multimetal oxide material M1 had the following gross stoichiometry:

$$Mo_{4.16}V_{1.15}W_{0.61}Cu_{0.61}Sb_{0.64}O_x \hat{=} [Mo_{12}V_{3.46}W_{1.38}O_x]_{0.33}$$
$$[Mo_{0.5}W_{0.5}Cu_1O_y]_{0.31}[CuSb_{2.15}O_z]_{0.3}.$$

The X-ray diffraction pattern of the multimetal oxide material M1 obtained contained the superposition of HT copper molybdate structure type, wolframite structure type and $CuSb_2O_6$ structure type. After the calcined material M1 had been milled, it was used in a rotating drum to coat nonporous steatite spheres having a rough surface and a diameter of from 4 to 5 mm in an amount of 60 g of active material per 400 g of steatite spheres with simultaneous addition of water (coating process according to DE-A 4 442 346). The coated catalyst SM1 obtained was then dried with air at 110° C.

Example 2
Preparation of Starting Material 1: as in Example 1.
Preparation of Starting Material 2:

946.0 g of $Sb_2O_3$ having an Sb content of 83.0% by weight were suspended in 4 l of water while stirring. 822.4 g of a 30% strength by weight aqueous $H_2O_2$ solution were added at room temperature (25° C.). Thereafter, the suspension was heated to 100° C. in the course of 1 hour with further stirring and was refluxed for 5 hours at this temperature. A solution of 595.6 g of $Cu(CH_3COO)_2 \cdot H_2O$ having a Cu content of 32.0% by weight in 4 l of water was then added to the aqueous suspension at 100° C. in the course of 30 minutes, the temperature of the total aqueous mixture decreasing to 60° C. At this temperature, 407.9 g of a 25% by weight aqueous ammonia solution were then added. Thereafter, the aqueous suspension was stirred for a further 2 hours at 80° C. and then cooled to room temperature (25° C.). Finally, the aqueous suspension was spray-dried (inlet temperature: 350° C., outlet temperature: 110° C.). In a rotary furnace (1.5 l internal volume) with a capacity of 50 l (S.T.P.)/h of air, the resulting spray-dried powder was heated stepwise, first to 150° C. in the course of 1 hour, then to 200° C. in the course of 4 hours and finally to 300° C. in the course of 2 hours, and was kept at the last-mentioned temperature for 1 hour. Thereafter, the powder obtained was heated to 400° C. in the course of 1.5 hours and was kept at this temperature for 1 hour. The powder obtained had a specific BET surface area of 48.5 m²/g and the composition $CuSb_{2.15}O_z$. The powder X-ray pattern of the powder obtained exhibited the fraction reflections of the mineral partzite and thus corresponded to reference spectrum 7-0303 of the JCPDS-ICDD index.
Preparation of Starting Material 3:

633.8 g of ammonium heptamolybdate tetrahydrate (81.8% by weight of $MoO_3$), 122.25 g of ammonium metavanadate (77.3% by weight of $V_2O_5$) and 107.0 g of ammonium paratungstate heptahydrate (89.0% by weight of $WO_3$) were dissolved in succession in 4660 g of water at 95° C. The aqueous solution (starting material 3) was thus based on the following elemental stoichiometry:

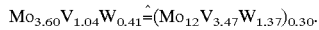

$$Mo_{3.60}V_{1.04}W_{0.41} \hat{=} (Mo_{12}V_{3.47}W_{1.37})_{0.30}.$$

Preparation of the Multimetal Oxide Material M2 and of the Coated Catalyst SM2:

The clear, orange solution obtained above (starting material 3) was cooled to 25° C., after which 105.3 g of 100% strength by weight acetic acid and 119.2 g of 25% strength by weight aqueous ammonia solution were then added in succession. 74.1 g of starting material 1 were stirred into the aqueous solution cooled to 25° C. and containing starting material 3, so that the molar ratio of the abovementioned stoichiometric units was 0.277 (starting material 1) to 0.30 (starting material 3). 116.86 g of starting material 2 were then added to the aqueous suspension containing starting materials 1 and 3, so that the molar ratio of the abovementioned stoichiometric units was 0.273 (starting material 2) to 0.30 (starting material 3). The resulting aqueous suspension was stirred for a further hour at 25° C. and then spray-dried (inlet temperature: 350° C., outlet temperature: 110° C.). The spray-dried powder was then kneaded with a mixture of 70% by weight of water and 30% by weight of acetic acid (0.35 kg of liquid/kg of spray-dried powder) (LUK 2.5 kneader from Werner & Pfleiderer, Stuttgart). The kneaded material obtained was dried for 16 hours at 110° C. in a through-circulation oven. The comminuted kneaded material was then calcined in an air/nitrogen mixture (40 l (S.T.P.)/h of air and 500 l (S.T.P.)/h of nitrogen) in a rotating tube (internal diameter 2.5 cm, heated length 51 cm). 700 g of material to be calcined were introduced into the heated length of the rotating tube. In the course of the calcination, the kneaded material was first heated to 325° C. in the course of 60 minutes, this temperature was then maintained for 4 hours, heating was then carried out to 400° C. in the course of 10 minutes and this temperature was maintained for 1 hour. The resulting multimetal oxide material M2 had the following gross stoichiometry:

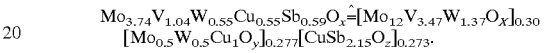

$$Mo_{3.74}V_{1.04}W_{0.55}Cu_{0.55}Sb_{0.59}O_x \hat{=} [Mo_{12}V_{3.47}W_{1.37}O_x]_{0.30}$$
$$[Mo_{0.5}W_{0.5}Cu_1O_y]_{0.277}[CuSb_{2.15}O_z]_{0.273}.$$

The X-ray diffraction pattern of the active material obtained contained the superposition of HT copper molybdate structure type, wolframite structure type and $CuSb_2O_6$ structure type. After the calcined active material had been milled, it was used to coat nonporous steatite spheres having a rough surface and a diameter of from 4 to 5 mm in amount of 60 g of active material per 400 g of steatite spheres with simultaneous addition of water (coating process according to DE-A 4 442 346). The coated catalyst SM2 obtained was then dried with air at 110° C.

Example 3
Associated Preparation of Starting Material 1 and Starting Material 2

366.2 g of $Sb_2O_3$ (Sb content: 83.0% by weight) were suspended in 4000 g of water while stirring. 421.6 g of a 30% strength by weight aqueous $H_2O_2$ solution were added at room temperature (25° C.). Thereafter, the suspension was heated to 100° C. in the course of 1 hour with further stirring and was refluxed at this temperature for 5 hours. A solution of 496.3 g of $Cu(CH_3COO)_2 \cdot H_2O$ (32.3% by weight of Cu) in 4000 g of water was then added in the course of 30 minutes to the aqueous suspension at 100° C., the temperature of the total aqueous mixture decreasing to 60° C. At this temperature, 340.0 g of 25% strength by weight aqueous ammonia solution were then added. The aqueous suspension was then stirred for 2 hours at 80° C. 110.3 g of $(NH_4)_6Mo_7O_{24} \cdot 4H_2O$ (81.5% by weight of $MoO_3$) and 161.8 g of $(NH_4)_{10}W_{12}O_{41} \cdot 7H_2O$ (89.5% by weight of $WO_3$) were then added. The resulting aqueous suspension was stirred for a further 20 hours at 80° C. and then spray-dried (inlet temperature: 350° C., outlet temperature: 110° C.). In a rotary furnace (1 l internal volume) with passage of 20 l (S.T.P.)/h of air, a part of the spray-dried powder obtained (about 200 g) was heated step-wise, first to 150° C. in the course of 1 hour, then to 200° C. in the course of 4 hours and then to 300° C. in the course of 2 hours, and was kept at the last-mentioned temperature for 1 hour. Heating was then carried out to 850° C. in the course of 2 hours and this temperature was maintained for 2 hours. The resulting powder had a specific BET surface area of 0.6 m²/g and the composition $Cu—Mo_{0.25}W_{0.25}Sb_1O_x$ (x≦5). The powder x-ray pattern of the powder obtained exhibited the diffraction reflections of $CuSb_2O_6$ (reference spectrum 17-0284 of the JCPDS-ICDD index) and the diffraction reflections of $CuWO_4$ (reference spectrum 21-0307 of the JCPDS-ICDD index).

Preparation of Starting Material 3:

790.4 g of ammonium heptamolybdate tetrahydrate (81.8% by weight of MoO$_3$), 152.3 g of ammonium metavanadate (77.3% by weight of V$_2$O$_5$) and 128.4 g of ammonium paratungstate heptahydrate (89.0% by weight of WO$_3$) were dissolved in succession in 5800 g of water at 95° C. The aqueous solution (starting material 3) was thus based on the following elemental stoichiometry:

$$Mo_{4.49}V_{1.29}W_{0.49} \hat{=} (Mo_{12}V_{3.45}W_{1.32})_{0.374}.$$

Preparation of the Multimetal Oxide Material M3 and of the Coated Catalyst SM3:

The clear, orange solution obtained above (starting material 3) was cooled to 25° C. and 150.0 g of ammonium acetate were added. 115.8 g of starting material (1+2) were stirred into the aqueous solution cooled to 25° C. and containing starting material 3, so that the molar ratio of the abovementioned stoichiometric units was 0.345 (starting material (1+2)) to 0.374 (starting material 3). The resulting aqueous suspension was stirred for a further hour at 25° C. and the aqueous mixture was then spray-dried (inlet temperature: 350° C., outlet temperature: 110° C.). The spray-dried powder was then kneaded with a mixture of 70% by weight of water and 30% by weight of acetic acid (0.35 kg of liquid/kg of a spray-dried powder) (LUK 2.5 kneader from Werner & Pfleiderer, Stuttgart). The kneaded material obtained was dried for 16 hours at 110° C. in a through-circulation drier. The comminuted kneaded material was calcined in a rotating tube (6.3 l internal volume) through which an air/nitrogen mixture (15 l (S.T.P)/h of air and 200 l (S.T.P.)/h of nitrogen) flowed. 700 g of material to be calcined were introduced into the rotating tube. In the course of the calcination, the kneaded material was first heated to 325° C. in the course of 60 minutes, this temperature was maintained for 4 hours, heating was then carried out to 400° C. in the course of 20 minutes and this temperature was maintained for 1 hour. The resulting catalytically active material had the following gross stoichiometry:

$$Mo_{4.57}V_{1.29}W_{0.58}Cu_{0.345}Sb_{0.345}O_x \hat{=} [Mo_{12}V_{3.45}W_{1.32}O_x]_{0.374}$$
$$[CuMo_{0.5}W_{0.5}O_y]_{0.1725}[CuSb_2O_z]_{0.1725}.$$

The X-ray diffraction pattern of the multimetal oxide material obtained contained the superposition of the HT copper molybdate structure type, of copper antimonate and of the wolframite structure type. After the calcined multimetal oxide material had been milled, it was used to coat nonporous steatite spheres having a rough surface and a diameter of from 4 to 5 mm in a rotating drum in an amount of 60 g of active powder per 400 g of steatite spheres with simultaneous addition of water (coating process according to DE-A 4 442 346). The coated catalyst SM3 obtained was then dried with air at 110° C.

Example 4

Associated Preparation of Starting Material 1 and Starting Material 2

The Preparation of the Starting Material (1+2) was Carried Out as in Example 3.

Preparation of Starting Material 3:

435.6 g of ammonium heptamolybdate tetrahydrate (81.8% by weight of MoO$_3$), 83.6 g of ammonium metavanadate (77.3% by weight of V$_2$O$_5$) and 73.1 g of ammonium paratungstate heptahydrate (89.0% by weight of WO$_3$) were dissolved in succession in 3210 g of water at 95° C. The aqueous solution (starting material 3) was thus based on the following elemental stoichiometry:

$$Mo_{2.48}V_{0.71}W_{0.28} \hat{=} (Mo_{12}V_{3.43}W_{1.35})_{0.207}.$$

Preparation of the Multimetal Oxide Material M4 and of the Coated Catalyst SM4:

The clear, orange solution obtained above (starting material 3) was cooled to 25° C. and 108.4 g of ammonium acetate were then added. 127.2 g of starting material (1+2) were stirred into the aqueous solution cooled to 25° C. and containing starting material 3, so that the molar ratio of the abovementioned stoichiometric units was 0.379 (starting material (1+2)) to 0.207 (starting material 3). The resulting aqueous suspension was stirred for a further hour at 25° C. and the aqueous mixture was then spray-dried (inlet temperature: 350° C., outlet temperature: 110° C.). The spray-dried powder was then kneaded with a mixture of 70% by weight of water and 30% by weight of acetic acid (0.35 kg of liquid/kg of a spray-dried powder) (LUK 2.5 kneader from Werner & Pfleiderer, Stuttgart). The kneaded material obtained was dried for 16 hours at 110° C. in a through-circulation drier. 700 g of a kneaded material prepared and dried in this manner were comminuted and were calcined in a rotating tube (6.3 l internal volume) through which an air/nitrogen mixture (15 l (S.T.P.)/h of air and 200 l (S.T.P.)/h of nitrogen) flowed. In the course of the calcination, the kneaded material was first heated to 325° C. in the course of 60 minutes, this temperature was then maintained for 4 hours and was then increased to 400° C. in the course of 20 minutes and this temperature was maintained for 1 hour. The resulting catalytically active multimetal oxide material M4 had the following gross stoichiometry:

$$Mo_{2.58}V_{0.71}W_{0.37}Cu_{0.379}SbO_x \hat{=} [Mo_{12}V_{3.43}W_{1.35}O_x]_{0.207}$$
$$[CuMo_{0.5}W_{0.5}O_y]_{0.189}[CuSb_2O_z]_{0.189}.$$

The X-ray diffraction pattern of the multimetal oxide material M4 obtained contained the superposition of the HT copper molybdate structure type, of copper antimonate and of the wolframite structure type. After the calcined multimetal oxide material M4 had been milled, it was used to coat nonporous steatite spheres having a rough surface and a diameter of from 4 to 5 mm in a rotating drum in an amount of 60 g of active powder per 400 g of steatite spheres with simultaneous addition of water (coating process according to DE-A 4 442 346). The coated catalyst SM4 obtained was then dried with air at 110° C.

Example 5

Preparation of Starting Material 1:

Starting Material 1 was Prepared as in Example 1.

Preparation of Starting Material 2:

946.05 g of Sb$_2$O$_3$ (Sb content of 83.0% by weight) were suspended in 4000 g of water while stirring. 822.4 g of a 30% strength by weight aqueous H$_2$O$_2$ solution were added at room temperature. The resulting aqueous suspension was heated to 100° C. in the course of 1 hour with further stirring and was refluxed at this temperature for 5 hours. A solution of 748.8 g of Ni(CH$_3$COO)$_2$·4H$_2$O (Ni content: 23.6% by weight) in 4000 g of water was then added in the course of 30 minutes to the aqueous suspension at 100° C., the temperature of the resulting total aqueous mixture decreasing to 60° C. At this temperature, 407.9 g of a 25% strength by weight aqueous ammonia solution were then added. Thereafter, the suspension was stirred for a further 2 hours at 80° C. and then cooled to room temperature (25° C.). The resulting aqueous suspension was then spray-dried (inlet temperature: 350° C., outlet temperature: 110° C.). In a rotary furnace. (1 l internal volume) with passage of air (20 l(S.T.P.)/h), 150 g of the spray-dried powder obtained were heated stepwise, first to 150° C. in the course of 1 hour, then to 200° C. in the course of 4 hours and then to 300° C. in the course of 2 hours, and kept at the last-mentioned temperature for 1 hour. Thereafter, heating was carried out to 800° C. in the course of 2 hours and this temperature was maintained for 2 hours. The resulting powder had a specific BET surface area of 0.9 m²/g and had the composition NiSb$_{2.15}$O$_x$ (x≦0.6375). The powder X-ray pattern of the powder obtained exhibited essentially the diffraction reflections of NiSb$_2$O$_6$ (reference spectrum 38-1083 of the JCPDS-ICDD index).

Preparation of Starting Material 3:

704.1 g of ammonium heptamolybdate tetrahydrate (81.8% by weight of MoO$_3$), 135.7 g of ammonium metavanadate (77.3% by weight of V$_2$O$_5$) and 118.77 g of ammonium paratungstate heptahydrate (89.0% by weight of WO$_3$) were dissolved in succession in 5190 g of water at 95° C. The aqueous solution (starting material 3) was thus based on the following elemental stoichiometry:

$$(Mo_{4.00}V_{1.15}W_{0.456}) \hat{=} (Mo_{12}V_{3.45}W_{1.37})_{0.333}.$$

Preparation of the Multimetal Oxide Material M5 and of the Coated Catalyst SM5:

The clear, orange solution obtained above (starting material 3) was cooled to 25° C. and 116.9 g of 100% strength acetic acid and 132.3 g of 25% strength ammonia solution were added in succession. 82.3 g of starting material 1 were stirred into the aqueous solution cooled to 25° C. and containing starting material 3, so that the molar ratio of the abovementioned stoichiometric units was 0.308 (starting material 1) to 0.333 (starting material 3). 130.0 g of starting material 2 were then added to the aqueous suspension which contained the starting materials 1 and 3, so that the molar ratio of the abovementioned stoichiometric units was 0.308 (starting material 2) to 0.333 (starting material 3). The resulting aqueous suspension was stirred for 1 hour at 25° C. and the aqueous mixture was then spray-dried (inlet temperature: 350° C., outlet temperature: 110° C.). The spray-dried powder was then kneaded with a mixture of 70% by weight of water and 30% by weight of acetic acid (0.35 kg of liquid/kg of spray-dried powder) (LUK 2.5 kneader from Werner & Pfleiderer, Stuttgart). The kneaded material obtained was dried for 16 hours at 110° C. in a through-circulation drier. The comminuted kneaded material was calcined in a rotating tube (6.3 l internal volume) through which an air/nitrogen mixture (15 l (S.T.P.)/h of air and 200 l (S.T.P.)/h of nitrogen) flowed. 700 g of material to be calcined were introduced into the rotating tube in the course of the calcination, the kneaded material was first heated to 325° C. in the course of 60 minutes, this temperature was maintained for 4 hours, heating was then carried out to 400° C. in the course of 20 minutes and this temperature was maintained for 1 hour. The resulting catalytically active multimetal oxide material M5 had the following gross stoichiometry:

$$Mo_{4.15}V_{1.15}W_{0.61}Cu_{0.308}Ni_{0.308}Sb_{0.662}O_x \hat{=} [Mo_{12}V_{3.45}W_{1.37}O_x]_{0.333}$$
$$[CuMo_{0.5}W_{0.5}O_y]_{0.308}[NiSb_{2.15}O_z]_{0.308}.$$

The X-ray diffraction pattern of the multimetal oxide material M5 obtained contained the superposition of the HT copper molybdate structure type, of nickel antimonate and of the wolframite structure type. After the calcined multimetal oxide material M5 had been milled, it was used to cool nonporous steatite spheres having a rough surface and a diameter of from 4 to 5 mm in a rotating drum in an amount of 60 g of active powder per 400 g of steatite spheres with simultaneous addition of water (coating process according to DE-A 4 442 346). The coated catalyst M5 obtained was then dried with air at 110° C.

Comparative Example 1

A comparative multimetal oxide material VM1 which had the same gross stoichiometry as the multimetal oxide material M1 was prepared by the following one-pot preparation method:

730.7 g of ammonium heptamolybdate tetrahydrate (81.8% by weight of MoO$_3$), 135.7 g of ammonium metavanadate (77.3% by weight of V$_2$O$_5$) and 160.3 g of ammonium paratungstate heptahydrate (89.0% by weight of WO$_3$) were dissolved in succession in 5460 g of water at 95° C. The clear, orange aqueous solution obtained was cooled to 25° C., and 116.5 g of 100% strength by weight acetic acid and 132.3 g of 25% strength by weight aqueous ammonia solution were added. 94.6 g of Sb$_2$O$_3$ having an Sb content of 83.0% by weight were stirred into the solution obtained. A solution of 120.8 g of copper acetate hydrate (32.0% by weight of Cu) was then added in a mixture of 800 g of water and 95.6 g of a 25% strength by weight aqueous ammonia solution.

The aqueous suspension obtained was stirred for a further hour at 25° C. and then spray-dried (inlet temperature: 350° C., outlet temperature: 110° C.). The spray-dried powder was then kneaded with dilute acetic acid, dried and calcined, these tests being carried out as in Example 1.

A coated catalyst SVM1 was then prepared from the comparative multimetal oxide material VM1 as in Example 1.

Comparative Example 2

Preparation of Starting Material 1:

The Preparation of Starting Material 1 was Carried Out as in Example 1.

Preparation of a Starting Material (2+3):

For the combined preparation of a starting material (2+3), 703.6 g of ammonium heptamolybdate tetrahydrate (81.8% by weight of MoO$_3$), 135.7 g of ammonium metavanadate (77.3% by weight of V$_2$O$_5$) and 120.3 g of ammonium paratungstate heptahydrate (89.0% by weight of WO$_3$) were dissolved in succession in 5260 g of water at 95° C., the aqueous solution was cooled to 25° C. and 116.9 g of 100% strength by weight acetic acid and 132.3 g of 25% strength by weight of aqueous ammonia solution were added in succession. 94.6 g of Sb$_2$O$_3$ having an Sb content of 83.0% by weight in 4000 g of water were suspended in the solution obtained. A solution of 59.6 g of copper acetate hydrate (32.0% by weight of Cu) in a mixture of 400 g of water and 40.8 g of 25% strength by weight aqueous ammonia solution was added to the resulting aqueous mixture.

Preparation of the comparative multimetal oxide material VM2 and of the comparative coated catalyst SVM2:

A comparative multimetal oxide material VM2 was prepared from starting material 1 and starting material (2+3) as follows:

82.3 g of the starting material 1 prepared in Example 1 were stirred into the aqueous mixture obtained above. The suspension obtained was stirred for a further hour at 25° C. and then spray-dried (inlet temperature: 350° C., outlet temperature: 110° C.). The spray-dried powder was then kneaded with dilute acetic acid, dried and calcined to give VM2 and the latter was processed to a coated catalyst SVM2, these tests being carried out as in Example 1.

Comparative Example 3

Preparation of Starting Material 2:

The Preparation of Starting Material 2 was Carried Out as in Example 1.

Preparation of a Starting Material (1+3):

For the combined preparation of a starting material (1+3), 730.7 g of ammonium heptamolybdate tetrahydrate (81.8% by weight of $MoO_3$), 135.7 g of ammonium metavanadate (77.3% by weight of $V_2O_5$) and 160.4 g of ammonium paratungstate heptahydrate (89.0% by weight of $WO_3$) were dissolved in succession in 5800 g of water at 95° C. The aqueous solution was cooled to 25° C., and 116.9 g of 100% strength by weight acetic acid and 132.3 g of 25% strength by weight aqueous ammonia solution were then added in succession. A solution of 61.2 g of copper acetate hydrate (40.0% by weight of CuO) in a mixture of 400 g of water and 54.8 g of a 25% strength by weight aqueous ammonia solution was then added to the resulting aqueous mixture.

Preparation of the comparative multimetal oxide material VM3 and of the comparative oated catalyst SVM3:

A comparative multimetal oxide material VM3 was prepared from starting material 2 and starting material (1+3) as follows:

129.7 g of the starting material 2 prepared in Example 1 were stirred into the aqueous mixture obtained above. The suspension obtained was stirred for a further hour at 25° C. and then spray-dried (inlet temperature: 350° C., outlet temperature: 110° C.). The spray-dried powder was then kneaded with dilute acetic acid, dried and calcined to give VM3 and the latter was converted into a coated catalyst SVM3, these tests being carried out as in Example 1.

b) Use of the coated catalysts from a) as catalysts for the gas-phase oxidation of acrolein to acrylic acid The coated catalysts were introduced into a tubular reactor (V2A stainless steel, 25 mm internal diameter, 2000 g catalyst bed, thermostatted by means of a salt bath) and a gaseous mixture having the composition 5% by volume of acrolein,
7% by volume of oxygen,
10% by volume of steam and
78% by volume of nitrogen was fed in at reaction temperatures of from 250 to 280° C. with the use of a residence time of 2.0 seconds. The salt bath temperature was adjusted in all cases so that, after forming was complete, a uniform acrolein conversion C of 99% resulted with a single pass. The product gas mixture flowing from the reactor was analyzed by gas chromatography. The results for the selectivity S of the acrylic acid formation for the use of the various catalysts are shown in the table below.

TABLE

| Catalyst | Salt bath temperature [°] | S % |
|---|---|---|
| SM1 | 270 | 96 |
| SM2 | 273 | 96 |
| SM3 | 281 | 93.8 |
| SM4 | 254 | 94.6 |
| SM5 | 267 | 95.0 |
| SVM1 | 268 | 93.7 |
| SVM2 | 266 | 95.5 |
| SVM3 | 266 | 94.8 |

We claim:

1. A multimetal oxide material of the formula I $$[A]_p[B]_q[C]_r \quad (I)$$

where

A is $Mo_{12}V_aX^1{}_bX^2{}_cX^3{}_dX^4{}_eX^5{}_fX^6{}_gO_x$,

B is $X^7{}_1Cu_hH_iO_y$,

C is $X^8{}_fSb_jH_kO_z$, $X^1$ is W, Nb, Ta, Cr and/or Ce, $X^2$ is Cu, Ni, Co, Fe, Mn and/or Zn, $X^3$ is Sb and/or Bi, $X^4$ is Li, Na, K, Rb, Cs and/or H, $X^5$ is Mg, Ca, Sr and/or Ba, $X^6$ is Si, Al, Ti and/or Zr, $X^7$ is Mo, W, V, Nb and/or Ta, $X^8$ is Cu, Ni, Zn, Co, Fe, Cd, Mn, Mg, Ca, Sr and/or Ba, a is from 1 to 8, b is from 0.2 to 5, c is from 0 to 23, d is from 0 to 50, e is from 0 to 2, f is from 0 to 5, g is from 0 to 50 h is from 0.3 to 2.5, i is from 0 to 2, j is from 0.05 to 50, k is from 0 to 50, x, y and z are numbers which are determined by the valency and frequency of the elements other than oxygen in (I) and p, q and r are numbers other than zero, with the proviso that the ratio p/(q+r) is from 20:1 to 1:20, and the ratio q/r is from 20:1 to 1:20, which contains the moiety $[A]_p$ in the form of three-dimensional regions A having the chemical composition $$Mo_{12}V_aX^1{}_bX^2{}_cX^3{}_dX^4{}_eX^5{}_fX^6{}_gO_x, \quad (A)$$

the moiety $[B]_q$ in the form of three-dimensional regions B having the chemical composition $$X^7{}_fCu_hH_iO_y \text{ and} \quad (B)$$

the moiety $[C]_r$ in the form of three-dimensional regions C having the chemical composition $$X^8{}_fSb_jH_kO_z \quad (C)$$

the regions A, B and C being distributed relative to one another in the same way as in a mixture comprising finely divided A, finely divided B and finely divided C.

2. A process for the preparation of a multimetal oxide material as claimed in claim 1, wherein a multimetal oxide material B $$X^7{}_fCu_hH_iO_y \quad (B)$$

as starting material 1 and a multimetal oxide material C $$X^8{}_fSb_jH_kO_z \quad (C)$$

as starting material 2 are preformed separately in finely divided form and the starting materials 1 and 2 are then brought into intimate contact with suitable sources of the elemental constituents of the multimetal oxide material A $$Mo_{12}V_aX^1{}_bX^2{}_cX^3{}_dX^4{}_eX^5{}_fX^6{}_gO_x, \quad (A)$$

in the desired ratio, and a resulting dry blend is calcined at from 250 to 500° C.

3. A process for the gas-phase catalytic oxidative preparation of acrylic acid from acrolein, which comprises carrying out the oxidative preparation with a multimetal oxide as claimed in claim 1 as the catalyst in contact with acrolein.

4. A process for the preparation of a multimetal oxide material as claimed in claim 1, wherein a multimetal oxide material B $$X^7_f Cu_h H_i O_y \tag{B}$$

as starting material 1 and a multimetal oxide material C $$X^8_t Sb_j H_k O_z \tag{C}$$

as starting material 2 are preformed in association with one another in finely divided form and the starting materials 1 and 2 are then brought into intimate contact with suitable sources of the elemental constituents of the multimetal oxide material A $$Mo_{12} V_a X^1_b X^2_c X^3_d X^4_e X^5_f X^6_g O_x, \tag{A}$$

in the desired ratio, and a resulting dry blend is calcined at from 250 to 500° C.

\* \* \* \* \*